US011135322B2

(12) United States Patent
Bhalla et al.

(10) Patent No.: US 11,135,322 B2
(45) Date of Patent: Oct. 5, 2021

(54) RADIOFLUORINATION METHOD

(71) Applicants: GE HEALTHCARE LIMITED, Buckinghamshire (GB); UNIVERSITY OF SOUTHAMPTON, Southampton Hamshire (GB)

(72) Inventors: Rajiv Bhalla, St. Lucia Brisbane (AU); Sajinder Kaur Luthra, Amersham (GB); Gill Reid, I, Southampton (GB); William Levason, Southampton (GB)

(73) Assignees: GE Healthcare Limited, Buckinghamshire (GB); University of Southampton, Hampshire (GB)

( * ) Notice: Subject to any disclaimer, the term of this patent is extended or adjusted under 35 U.S.C. 154(b) by 247 days.

(21) Appl. No.: 14/373,413

(22) PCT Filed: Jan. 22, 2013

(86) PCT No.: PCT/EP2013/051154
§ 371 (c)(1),
(2) Date: Jul. 21, 2014

(87) PCT Pub. No.: WO2013/110615
PCT Pub. Date: Aug. 1, 2013

(65) Prior Publication Data
US 2014/0377178 A1 Dec. 25, 2014

Related U.S. Application Data

(60) Provisional application No. 61/589,972, filed on Jan. 24, 2012.

(30) Foreign Application Priority Data

Jan. 23, 2012 (GB) .................................. 1201062

(51) Int. Cl.
*A61K 51/00* (2006.01)
*A61M 36/14* (2006.01)
*A61K 51/08* (2006.01)
*A61K 51/04* (2006.01)

(52) U.S. Cl.
CPC .......... *A61K 51/08* (2013.01); *A61K 51/0482* (2013.01); *A61K 51/082* (2013.01); *A61K 51/085* (2013.01)

(58) Field of Classification Search
CPC .. A61K 51/08; A61K 51/0482; A61K 51/082; A61K 51/085
USPC ....................................................... 424/1.69
See application file for complete search history.

(56) References Cited

U.S. PATENT DOCUMENTS

| | | | |
|---|---|---|---|
| 6,183,744 B1 | 2/2001 | Goldenberg | |
| 2008/0305042 A1* | 12/2008 | Gacek et al. | ................ 424/1.89 |
| 2009/0245130 A1 | 10/2009 | Bing | |
| 2011/0110854 A1 | 5/2011 | McBride et al. | |

FOREIGN PATENT DOCUMENTS

| | | |
|---|---|---|
| CN | 101854957.0 A | 10/2010 |
| CN | 102918031.0 A | 2/2013 |
| EP | 969866.0 A1 | 1/2000 |
| EP | 2806901 B1 | 3/2016 |
| EP | 2991969.0 A1 | 3/2016 |
| JP | 2010-515732 A | 5/2005 |
| JP | 2011507863.0 A | 3/2011 |
| JP | 2011-523697 A | 8/2011 |
| JP | 2015505533.0 A | 2/2015 |
| WO | 89/01475 | 2/1989 |
| WO | 2006/138357 | 12/2006 |
| WO | 2009079024 | 6/2009 |
| WO | 2010/114308 | 10/2010 |
| WO | 2011/068965 A1 | 6/2011 |
| WO | 2012082618.0 A1 | 6/2012 |
| WO | WO 2012082618 A2 * | 6/2012 |
| WO | 2013/110615 A1 | 8/2013 |
| WO | 2014177689.0 A1 | 6/2014 |

OTHER PUBLICATIONS

Willey et al. Main Group Met. Chem. 1999, 22, 515-518.*
Tredget et al. Organometall. 2005, 24, 3136-3148.*
Hudnall et al. J. Fluorine Chem. 2008, 131, 1182-1186.*
Martin, B., Coordin. Chem. Rev. 1996, 141,23-32.*
Clarke et al. Inorg. Chim. Acta 1991,181,273-280.*
Pandey et al. J. Med. Chem. 2005, 48, 6286-6295.*
Penkert et al. Chem. Commun. 1998, 557-558.*
Shetty et al. Chem. Commun. 2011, 47, 9732-9734.*
Great Britain Search Reports 1201062.5 dated May 8, 2012 and Jul. 9, 2012.
PCT/EP2013/051154 ISRWO dated Apr. 24, 2013.
Hejalea, et.al. Journal of Organometallic Chemistry, vol. 532, No. 1-2 Apr. 1, 1997 pp. 45-53.
Tredget, et.al. Organometallics, vol. 24 (13) 2005 pp. 3136-3148.
Willey, et.al. Polyehdron, vol. 20(5), 2001, pp. 423-429.
M. Eigen, "Fast Elementary Steps in Chemical Reaction Mechanisms," Pure and Applied Chemistry, vol. 6, pp. 97-115, 1963.
Japanese Office action in corresponding Japanese Application No. 2014-552659 (English Translation).
D'Souza, Christopher A. et al., High-Yielding Aqueous 18F-Labeling of Peptides via Al 18F Chelation, Bioconjugate Chemistry, 2011, vol. 22, No. 9, p. 1793-1803.

(Continued)

*Primary Examiner* — Michael G. Hartley
*Assistant Examiner* — Sean R Donohue
(74) *Attorney, Agent, or Firm* — Jeff B. Vockrodt; Culhane Meadow, PLLC

(57) ABSTRACT

The present invention relates to a method of labelling biological molecules with $^{18}F$, via attachment to fluorine to a macrocyclic metal complex of a non-radioactive metal, where the metal complex is conjugated to the biological molecule. Also provided are pharmaceutical compositions, kits and methods of in vivo imaging.

19 Claims, 2 Drawing Sheets

(56) References Cited

OTHER PUBLICATIONS

Kirk, A. D. et al., Synthesis of Cr(tacn)X3 (tacn=1, 4, 7-Triazacyclononane). Photochemistry and Emission Properties of the Triisothiocyanate, Inorganic chemistry, 1988, vol. 27, No. 6, p. 1095-1099.
Chinese Search Report in corresponding Chinese Appl. No. 201380015583.9 (English Translation).
International Preliminary Report on Patentability Received for PCT Application No. PCT/EP2013/051154, dated Jul. 29, 2014, 4 Pages.
Office Action Received for Chinese Patent Application No. 201380015583.9, dated Mar. 7, 2017, 16 Pages (10 pages English Translation + 6 Pages official copy).
Ward M.D, "The Coordination Chemistry of Macrocyclic Ligands", School of Chemistry, Cantock's Close, Bristol, BS8, 1 TS, Jan. 1, 1990, pp. 303-305.
Amin et al. "Synthesis and characterization of the yttrium(III) and lutetium(III) complexes of 1,4,7-tris carbamoylmethyl)-1,4,7-triazacyclononane (TCMT). Crystal structure of [Y(TCMT)(CF3SO3)2(H2O)]{CF3SO3}", Inorganica Chimica Acta, 1996, vol. 246, pp. 99-107.
Barthomola et al. "Technetium and Gallium Derived Radiopharmaceuticals: Comparing and Contrasting the Chemistry of Two Important Radiometals for the Molecular Imaging Era", Chemical Reviews, vol. 110, Issue 5, 2010, pp. 2903-2920.
Brechbiel, M. W., "Bifunctional Chelates for Metal Nuclides", Quarterly Journal of Nuclear Medicine and Molecular Imaging, vol. 52, Issue 2, 2008, 166-173.
Chakraborty et al. "99mTc and 111 In-Labeling of Small Biomolecules: Bifunctional Chelators and Related Coordination Chemistry", Current Topics in Medicinal Chemistry, vol. 10, Issue 11, 2010, pp. 1113-1134.
Office Action Received for Chinese Patent Application No. 201480024885. 7, dated Nov. 28, 2016, 14 pages 8 Pages of English Translation+ 6 pages official copy.
Clezy et al., "The Chemistry of Pyrrolic Compounds. LXI. Petroporphyrins From the Julia Creek Oil Shale: Further evidence for the Derivation of Etiotype Petroporphyrins From Chlorophyll", Australian Journal of Chemistry, vol. 42, ssue 6, 1989, pp. 775-786.
Davies et al., "Divergent Pathways in the Intramolecular Reactions between Rhodium-Stabilized Vinylcarbenoids and Pyrroles: Construction of Fused Tropanes and 7-Azabicyclo[4.2.0]octadienes", Journal of Organic Chemistry, 1996, vol. 61, pp. 2305-2313.
Dixit et al. "Characterization of a cDNA Encoding the Heparin and Collagen Binding Domains of Human Irhrombospondin", Proceedings of the National Academy of Sciences, vol. 83, 1986, pp. 5449-5453.
Doolittle, Russell F., "Fibrinogen and Fibrin", Annual Review of Biochemistry, vol. 53, 1984, pp. 195-229.
Office Action in EP 14723396.9-1112 dated Jan. 29, 2018.
Flassbeck et al. "Synthese van N-phenolat-funktionalisierten Makrocyclen des 1,4,7-Trazacyclononans sowie des 1-Oxa-4,7-diazacyclononans und ihre Komplexchemie mit Eisen(III)", Journal of Inorganic and General Chemistry, vol. 608, Issue No. 2, 1992, pp. 60-68.
Goodman et aL, "Structure-Activity Relationship of a Bitter Diketopiperazine Revisited", Biopolymers, vol. 24, 1985, 37 pages.
Gutman et al., "Human Fibronectin is Synthesized as a Prepropolypeptide", FEBS Letters, vol. 207, No. 1, 1986, pp. 145-148.
Hansson et al., "Structure of the Human Beta-Casein Encoding Gene", Gene, vol. 139, Issue 2, 1994, pp. 193-199.
Hjelstuen et al. "Standardization of Fluorine-18 Manufacturing Processes: New Scientific Challenges for PET", vol. 178, Issue 3, 2011, pp. 307-313.
Jacobson et al. "PET Designated Flouride-18 Production and Chemistry", Current Topics in Medicinal Chemistry, 2010, vol. 10, No. 11, pp. 1048-1059.
Japan Notice of Preliminary Rejection for Japanese Patent Application No. 2016-511091, dated Feb. 13, 2018, 4 pages.

Japan Notice of Preliminary Rejection for Japanese Patent Application No. 2016-511091, dated Apr. 4, 2019.
Kuppers et al., "Electron-transfer barriers in cobalt(III) and cobalt(II) bis complexes of 1,4,7-triazacyclononane (tacn) and 1,4,7-trithiacyclononane (ttcn). Crystal structures of [CoII(tacn)2]12.H2O and of [CoIII(ttcn)2](ClO4)3", Inorganic Chemistry, vol. 25, Issue 14, 1986, pp. 2400-2408.
Laverman etal. J. Nucl. Med. 2010, 51, 454-461.
Lloyd-Williams et al., "Chemical Approaches to the Synthesis of Peptides and Proteins", CRC Press, 1997.
Mahapatra et al., "Structural, Spectroscopic, and Theoretical Characterization of Bis(μ-oxo)dicopper Complexes, 25 Novel Intermediates in Copper-Mediated Dioxygen Activation", Journal of the American Chemical Society, vol. 118, ssue 46, 1996, pp. 11555-11574.
Martin et al., "Synthesis of Selectively Protected tri- and Hexaamine Macrocycles", Journal of Organic Chemistry, vol. 47, Issue 3, 1982, pp. 412-415.
McBride, William J., et al., "A Novel Method of 18F Radiolabeling for PET," The Journal of Nuclear Medicine, May 4, 2009, pp. 991-998.
McBride et al—"Improved 18F Labeling of Peptides with a Fluoride-Aluminum-Chelate Complex", Bioconjugate Chem, 2010, vol. 21, Issue No. 7 pp. 1331-1340.
McBride et al. "Radiofluorination using aluminum-fluoride (Al18F)", EJNMMI Research, 3(1):36-47 (May 8, 2013).
McBride et aL, "The Radiolabeling of Proteins by the [18F]AIF Method", Applied Radiation and Isotopes, vol. 70, 2012, pp. 200-204.
Morgan et aL, Drug News & Perspectives, vol. 12, No. 3, 1999, pp. 137-145-.
Pasqualini et al., "av Integrins as Receptors for Tumor Targeting by Circulating Ligands", Nature Biotechnology, vol. 5. Issue 6, 1997, pp. 542-546.
Plush, Sally, et al., "Aminoacid N-substituted 1,4, 7-triazacyclononane and 1,4, 7, 10-tetraazacyclododecane Zn2+, 2 Cd2+ and Cu2+ complexes. A preparative, potentiometric titration and NMR spectroscopic study," Dalton ☐ Irransactions, 2004, pp. 1410-1417.
Ruoslahti E, "Integrins as Signaling Molecules and Targets for Tumor Therapy", Kidney International, 1997, vol. 51, Issue 5, pp. 1413-1417.
Satyamurthy et al., "Electronic Generators for the Production of Positron-Emitter Labeled Radiopharmaceuticals: Where Would PET Be Without Them?", Clinical Positron Imaging, 1999, vol. 2, Issue No. 5, pp. 233-253.
Shetty et al. Eur. J. Inorg. Chem. 2010, 5432-5438.
Schirrmacher et al. "Recent Developments and Trends in 18F-Radiochemistry: Syntheses and Applications", Mini-Reviews in Organic Chemistry, 2007, pp. 317-329.
Smith et al. "Inorganic approaches for radiolabelling biomolecules with fluorine-18 for imaging with Positron Emission Tomography", Dalton Transactions, 2011, vol. 40, Issue 23, pp. 6196-6205.
Tolmachev, Vladimir, et al., "Evaluation of a Maleimido Derivative of NOTA for Site-Specific Labeling of Affibody Molecules," Bioconjugate Chemistry, 2011, 22, pp. 894-902.
Tone et al, "Structure of Human a2-plasmin Inhibitor Deduced from the cDNA Sequence 1", J Biochem, vol. 102, Issue 5, 1987, pp. 1033-1041.
Wadas et al. Chem. Rev. 2010, 110, 2858-2902.
Weighardt et al. "C2-Symmetric 1,4-Diisopropyl-7-R-1,4,7-Triazacyclononanes", Inorganic Syntheses, 1998, vol. B2, pp. 75-81.
Weyhermuller et al., "Nitrogen versus oxygen co-ordination of carboxamide-functionalized triazacyclononane ligands in transition metal ion complexes", Journal of the Chemical Society, Dalton Transactions, Issue 22, 1998, pp. 805-3814.
Weighardt et al., "New triply hydroxo-bridged complexes of chromium(III), cobalt(III), and rhodium(III): crystal Structure of tris(.mu.-hydroxo)bis[(1,4,7-trimethyl-1,4,7-
triazacyclononane)chromium(III)] triiodide trihydrate", Inorganic Chemistry, vol. 21, 1982, pp. 3086-3090.
Zhang et al. "Metal ion promoted hydrolysis of nitrile-functionalized triazamacrocycle", Inorganic Chemistry Communications, vol. 9, Issue 3, 2006, pp. 269-272.
Chinese Office Action received in Application No. 201811135640.8 dated Nov. 4, 2020, 16 pages.

(56) References Cited

OTHER PUBLICATIONS

Chinese Search Report received in Application No. 201811135640.8 dated Oct. 27, 2020, 2 pages.
Tredget, et al., "A Family of Scandium and Yttrium Tris ((trimethylsilyl)methyl) Complexes with Neutral N3 Donor Ligands," Organometallic 2005, 24, 3136-3148, received Mar. 19, 2005, 13 pages.
Ward, "The Coordination Chemistry of Macrocyclic Ligands," View Article Online / Journal Homepage / Table of Contents for this issue, School of Chemistry, Cantock's Close, Bristol, Oct. 23, 2020, 37 pages.

* cited by examiner

Figure 1: X-ray structure of AlCl₃(Me₃-tacn)].
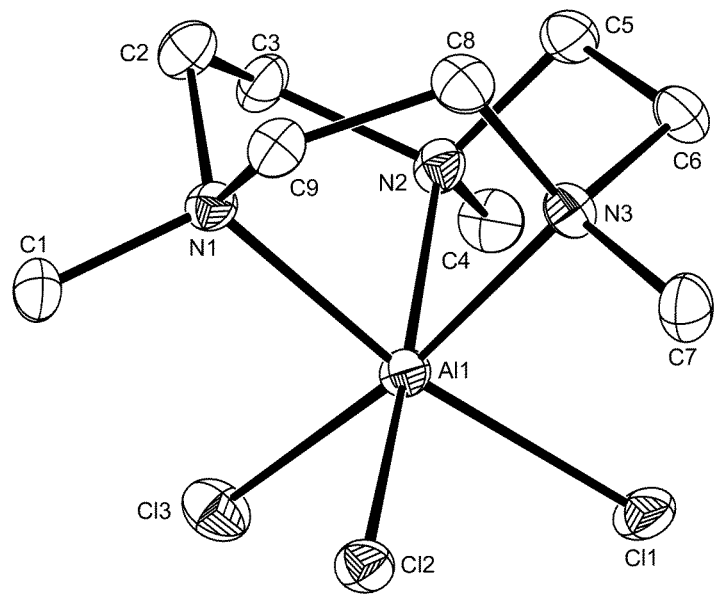
Figure 2: X-ray Structure of [GaCl₃(Me₃-tacn)]
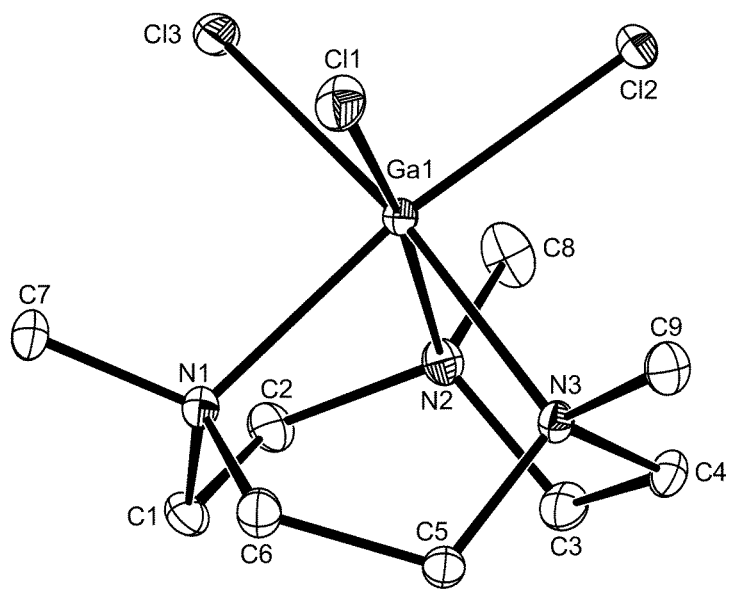

Figure 3: X-ray structure of [GaF$_3$(Me$_3$-tacn)].
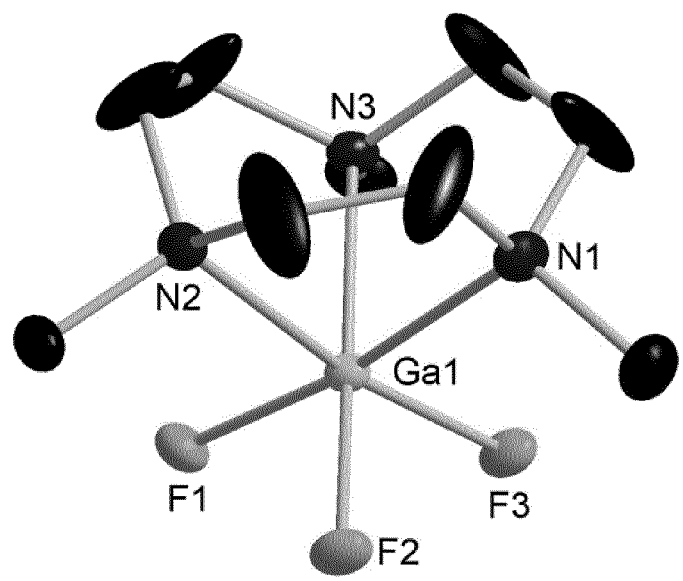

RADIOFLUORINATION METHOD

This application is a filing under 35 U.S.C. 371 of international application number PCT/EP2013/051154, filed Jan. 22, 2013, which claims priority to Great Britain application number 1201062.5 filed Jan. 23, 2012 and to U.S. application No. 61/589,972 filed Jan. 24, 2012, the entire disclosure of each of which is hereby incorporated by reference.

FIELD OF THE INVENTION

The present invention relates to a method of labelling biological molecules with $^{18}$F, via attachment to fluorine to a macrocyclic metal complex of a non-radioactive metal, where the metal complex is conjugated to the biological molecule. Also provided are pharmaceutical compositions, kits and methods of in vivo imaging.

BACKGROUND TO THE INVENTION

The $^{18}$F radiolabelling of biological molecules, to obtain radiotracers suitable for in vivo imaging is an area of continued interest [Schirrmacher et al. Mini-Rev. Org. Chem., 4(4), 317-329 (2007)]. Whilst there are many methods for direct (single-step) labelling of small molecules with $^{18}$F, these methods are generally not suitable for application to peptides (and larger macromolecules). The presence of amino acids such as lysine and arginine make standard strategies of incorporation of fluoride via nucleophilic substitution difficult, due to:
 (i) hydrogen bonding interactions between the fluoride and these amino acid functionalities, thus reducing the nucleophilicity of the fluoride ion; and/or
 (ii) the requirement to use higher temperatures which can cause the degradation or disruption of the peptide/protein structure.

Inorganic chemistry approaches to improved radiofluorination methods have been reviewed by Smith et at [Dalton Trans., 40, 6196-6205 (2011)].

WO 2009/079024 (McBride et al) discloses an 'inorganic' method of labeling a molecule with $^{18}$F comprising:
 a) reacting the $^{18}$F with a metal to form an $^{18}$F metal complex; and
 b) attaching the $^{18}$F metal complex to a molecule to form one or more $^{18}$F labeled molecules to be administered to a subject.

WO 2009/079024 teaches that suitable metals for the metal complex are selected from aluminium, gallium, indium, lutetium and thallium.

Example 3 of WO 2009/079024 provides the $^{18}$F-labelling of various metal complexes of the chelate-peptide conjugate IMP 272:
 DOTA-Gln-Ala-Lys(HSG)-D-Tyr-Lys(HSG)-NH$_2$
 IMP 272
 where DOTA=1,4,7,10-tetraazacyclododecanetetraacetic acid,
 HSG=the histamine succinyl glycyl group.

The $^{18}$F-radiolabelling results reported were: indium (24%), gallium (36%), zirconium (15%), lutetium (37%) and yttrium (2%).

WO 2011/068965 discloses a method of labeling a molecule with $^{18}$F or $^{19}$F comprising attaching a complex of $^{18}$F or $^{19}$F and a group IIIA metal to a chelating moiety, wherein the chelating moiety is conjugated to the molecule or the chelating moiety is later attached to the molecule. WO 2011/068965 states that the metals of group IIIA (aluminium, gallium, indium, and thallium) are suitable for F binding, but that aluminium is preferred.

McBride et at subsequently reported [J. Nucl. Med., 50(6), 991-998 (2009) at page 994] that Ga, In, Zr, Lu and Y do not bind the IMP 272 peptide as well as the aluminium complex, and that the metal complexes of the alternative metals (Ga, In, Zr, Lu and Y) were unstable in water.

More recent publications have focused on aluminium as the metal of choice since the aluminium-fluoride bond is one of the strongest metal-fluoride bonds, and the AlF$_n$ complex is stable in vivo—and optimizing the aluminium chelator used [McBride et al, Bioconj. Chem., 21(7), 1331-1340 (2010); Bioconj. Chem., 22, 1793-1803 (2011) and Appl. Rad. Isot., 70, 200-204 (2012)]. Preferred chelators are based on the NODA system, with NODA-MPAEM used to conjugate to biomolecules:

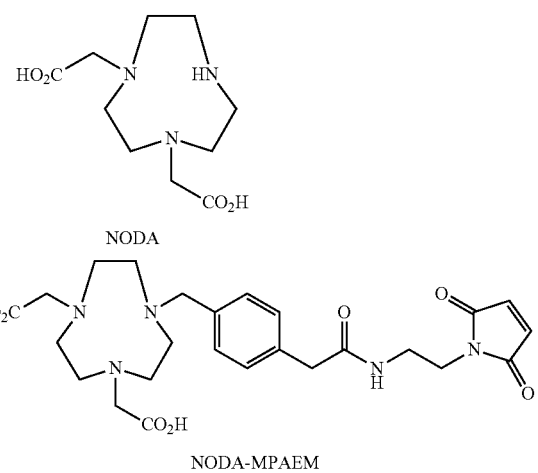

The prior art methods of WO 2009/079024, WO 2011/068965 and associated publications do, however have some disadvantages:
 (a) the kinetics of formation of the Al—$^{18}$F bond requires the use of higher temperatures for $^{18}$F-radiolabelling, and many biomolecules are temperature-sensitive;
 (b) the pH range (pH 3.8 to 4.2) for $^{18}$F-radiolabelling these metal complexes is relatively narrow, due to the need to avoid hydrolysis of the aluminium. This will not be compatible with all biomolecules due to acid-sensitive instability or risks of aggregation.

There is therefore still a need for alternative $^{18}$F-radiolabelling methods which permit efficient radiofluorination of a range of biological molecules, under mild conditions (of e.g. temperature and pH). Ideally such methods are suitable for aqueous conditions—since $^{18}$F is typically available as an aqueous solution and some biomolecules may not tolerate organic solvents. The capability of performing the labelling in aqueous or predominantly aqueous conditions, will eliminate the requirement to dry the [$^{18}$F] fluoride, which is typically required for traditional $^{18}$F chemistries involving "nucleophilic substitution". This has the benefit that it may further simplify the process of $^{18}$F process chemistry via a reduction of process steps. Reduction of process steps and in particular, the reduction of the radiosynthesis time has benefit in minimising loss of yield due to radioactive decay.

The Present Invention.

The present invention provides a versatile method for radiolabelling biomolecules, and in particular peptides:

(i) at lower temperatures (preferably room temperature);
(ii) in aqueous (or predominantly aqueous) conditions;
(iii) in a pH range which can be adjusted or adapted to match the properties of the peptide;
(iv) where the $^{18}$F-labelled agents exhibit high in vivo stability.

The present inventors have found that both the choice of metal ion and chelate scaffold are critical in the design of high affinity fluoride binders. The metal ions and the metal complexes of the present invention have several advantages:

(a) the metal ion exhibits a high affinity for fluoride in water and at medium pH;
(b) the metal centre has a preferred coordination number and limited redox ability—which simplifies the speciation and chemistry;
(c) the kinetics of substitution of the ligand being replaced by fluoride ion are fast enough (and sufficiently complete) to take up fluoride in the time available (based upon the half-life of $^{18}$F), but the resulting metal fluoride bond is sufficiently strong that metal-bound fluoride is not easily lost in purification or in vivo;
(d) the precursor for $^{18}$F labelling is a single, well-defined species which can be readily synthesized and purified.

The above characteristics of the metal complexes of the present invention mean that the non-radioactive metal complex of interest can be conjugated to the biological targeting moiety, and purified as necessary before the $^{18}$F-radiofluorination step. That is advantageous over prior art approaches for the reasons described above.

The present inventors have found that, for the metal complexes of the chelate systems described in the invention, the gallium and indium complexes are more suitable than their aluminium counterpart. For the chelate constructs described in this invention, the Ga(III) and In(III) chloride complexes are significantly more hydrolytically stable than their Al(III) analogues. In addition, the Ga(III) and In(III) fluoride complexes form at room temperature in both MeCN and H$_2$O solvents using tetraalkylammonium fluoride as the F$^-$ source or alternatively using aqueous KF as the F$^-$ source, and are hydrolytically stable. In contrast, the chloride/fluoride exchange does not occur at room temperature with the Al(III) complexes using tetraalkylammonium fluoride as the F$^-$ source in pure MeCN. This is an important difference in reactivity between the Ga(III) and Al(III) complexes and is believed likely to result from the smaller ionic radius of Al(III) vs. Ga(III).

DETAILED DESCRIPTION OF THE INVENTION

In a first aspect, the present invention provides an imaging agent which comprises an $^{18}$F-labelled compound of Formula I:

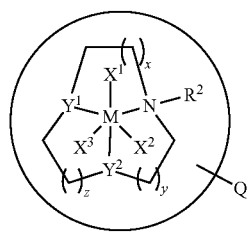

(I)

where:
Y$^1$ and Y$^2$ are independently O or NR',
X$^1$, X$^2$ and X$^3$ are independently Br, Cl, $^{19}$F or $^{18}$F,
 with the proviso that at least one of X', X$^2$ and X$^3$ is 18F;
x, y and z are independently 0, 1 or 2;
M is Al$^{3+}$, Ga$^{3+}$, In$^{3+}$, Sc$^{3+}$, Y$^{3+}$, Ho$^{3+}$, Er$^{3+}$, Tm$^{3+}$, Yb$^{3+}$ or Lu$^{3+}$;
R$^1$ is C$_{1-3}$ alkyl or —CH$_2$—Ar$^1$, wherein Ar$^1$ is C$_{5-12}$ aryl or C$_{3-12}$ heteroaryl;
R$^2$ is R$^1$ or Q;
Q is -L-[BTM], and may be present or absent; when present it is either R$^2$ or is attached at one of the carbon atoms of the —(CH$_2$)(CH$_2$)$_x$—, —(CH$_2$)(CH$_2$)$_y$— or —(CH$_2$)(CH$_2$)$_z$— groups;
L is a synthetic linker group of formula -(A)$_m$- wherein each A is independently —CR$_2$—, —CR=CR—, —CC—, —CR$_2$CO$_2$—, —CO$_2$CR$_2$—, —NRCO—, —CONR—, —CR=N—O—, —NR(C=O)NR—, —NR(C=S)NR—, —SO$_2$NR—, —NRSO$_2$—, —CR$_2$OCR$_2$—, —CR$_2$SCR$_2$—, —CR$_2$NRCR$_2$—, a C$_{4-8}$ cycloheteroalkylene group, a C$_{4-8}$ cycloalkylene group, —Ar—, —NR—Ar—, —O—Ar—, —Ar—(CO)—, an amino acid, a sugar or a monodisperse polyethyleneglycol (PEG) building block,
 wherein each R is independently chosen from H, C$_{1-4}$ alkyl, C$_{2-4}$ alkenyl, C$_{2-4}$ alkynyl, C$_{1-4}$ alkoxyalkyl or C$_{1-4}$ hydroxyalkyl;
m is an integer of value 1 to 20;
each Ar is independently a C$_{5-12}$ arylene group, or a C$_{3-12}$ heteroarylene group; BTM is a biological targeting moiety.

The imaging agents of the first aspect comprise a metal complex of a non-radioactive trivalent metal ion (M), i.e. where the metal is in the M(III) oxidation state. By the term "metal complex" is meant a coordination complex of a non-radioactive metal. Preferred such complexes comprise a chelating agent. Suitable non-radioactive metals of the invention (M) include aluminium, gallium, indium, scandium, yttrium, holmium, erbium, terbium, ytterbium or lutetium.

By the term "imaging agent" is meant a compound suitable for imaging the mammalian body. Preferably, the mammal is an intact mammalian body in vivo, and is more preferably a human subject. Preferably, the imaging agent can be administered to the mammalian body in a minimally invasive manner, i.e. without a substantial health risk to the mammalian subject when carried out under professional medical expertise. Such minimally invasive administration is preferably intravenous administration into a peripheral vein of said subject, without the need for local or general anaesthetic.

The term "in vivo imaging" as used herein refers to those techniques that non-invasively produce images of all or part of an internal aspect of a mammalian subject. A preferred imaging technique of the present invention is positron emission tomography (PET).

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components' being present.

By the term "biological targeting moiety" (BTM) is meant a compound which, after administration, is taken up selectively or localises at a particular site of the mammalian body in vivo. Such sites may for example be implicated in a particular disease state or be indicative of how an organ or metabolic process is functioning.

When Q is absent, $R^2$ is an $R^1$ group. When Q is present, it is either $R^2$ or is a backbone substituent at one of the carbon atoms of the —$(CH_2)(CH_2)_x$—, $(CH_2)(CH_2)_y$— or —$(CH_2)(CH_2)_z$— groups. For example, when x=1, the —$(CH_2)(CH_2)_x$— group with a Q substituent could be —(CHQ)(CH_2)— or —(CH_2)(CHQ)—.

Preferred Embodiments

Q is preferably present. More preferably Q is present and $R^2$=Q.

The BTM may be of synthetic or natural origin, but is preferably synthetic. The term "synthetic" has its conventional meaning, i.e. man-made as opposed to being isolated from natural sources eg. from the mammalian body. Such compounds have the advantage that their manufacture and impurity profile can be fully controlled. Monoclonal antibodies and fragments thereof of natural origin are therefore outside the scope of the term 'synthetic' as used herein. The molecular weight of the BTM is preferably up to 30,000 Daltons. More preferably, the molecular weight is in the range 200 to 20,000 Daltons, most preferably 300 to 18,000 Daltons, with 400 to 16,000 Daltons being especially preferred. When the BTM is a non-peptide, the molecular weight of the BTM is preferably up to 3,000 Daltons, more preferably 200 to 2,500 Daltons, most preferably 300 to 2,000 Daltons, with 400 to 1,500 Daltons being especially preferred.

The biological targeting moiety preferably comprises: a 3-100 mer peptide, peptide analogue, peptoid or peptide mimetic which may be a linear or cyclic peptide or combination thereof; a single amino acid; an enzyme substrate, enzyme antagonist enzyme agonist (including partial agonist) or enzyme inhibitor; receptor-binding compound (including a receptor substrate, antagonist, agonist or substrate); oligonucleotides, or oligo-DNA or oligo-RNA fragments. The enzyme and/or receptor is preferably endogenous to the mammalian subject.

By the term "peptide" is meant a compound comprising two or more amino acids, as defined below, linked by a peptide bond (ie. an amide bond linking the amine of one amino acid to the carboxyl of another). The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. The term "peptide analogue" refers to peptides comprising one or more amino acid analogues, as described below. See also *Synthesis of Peptides and Peptidomimetics*, M. Goodman et al, Houben-Weyl E22c, Thieme.

By the term "amino acid" is meant an L- or D-amino acid, amino acid analogue (eg. naphthylalanine) or amino acid mimetic which may be naturally occurring or of purely synthetic origin, and may be optically pure, i.e. a single enantiomer and hence chiral, or a mixture of enantiomers. Conventional 3-letter or single letter abbreviations for amino acids are used herein. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsi-peptides, retro-inverso peptides, thioamides, cycloalkanes or 1,5-disubstituted tetrazoles [see M. Goodman, Biopolymers, 24, 137, (1985)]. Radiolabelled amino acids such as tyrosine, histidine or proline are known to be useful in vivo imaging agents.

When the BTM is an enzyme substrate, enzyme antagonist, enzyme agonist, enzyme inhibitor or receptor-binding compound it is preferably a non-peptide, and more preferably is synthetic. By the term "non-peptide" is meant a compound which does not comprise any peptide bonds, ie. an amide bond between two amino acid residues. Suitable enzyme substrates, antagonists, agonists or inhibitors include glucose and glucose analogues; fatty acids, or elastase, Angiotensin II or metalloproteinase inhibitors. The enzyme of the enzyme substrate, antagonist, agonist or inhibitor is preferably endogenous to the mammalian subject. Suitable synthetic receptor-binding compounds include estradiol, estrogen, progestin, progesterone and other steroid hormones; ligands for the dopamine D-1 or D-2 receptor, or dopamine transporter such as tropanes; and ligands for the serotonin receptor. The receptor of the receptor-binding compound is preferably endogenous to the mammalian subject.

The BTM is most preferably a 3-100 mer peptide or peptide analogue. When the BTM is a peptide, it is preferably a 4-30 mer peptide, and most preferably a 5 to 28-mer peptide.

When the BTM is an enzyme substrate, enzyme antagonist, enzyme agonist or enzyme inhibitor, preferred such biological targeting molecules of the present invention are synthetic, drug-like small molecules i.e. pharmaceutical molecules. Preferred dopamine transporter ligands such as tropanes; fatty acids; dopamine D-2 receptor ligands; benzamides; amphetamines; benzylguanidines, iomazenil, benzofuran (IBF) or hippuric acid. Tropane agents are described by Morgan and Nowotnik [Drug News Perspect., 12(3), 137-145 (1999).

When the BTM is a peptide, preferred such peptides include:
somatostatin, octreotide and analogues,
peptides which bind to the ST receptor, where ST refers to the heat-stable toxin produced by *E. coli* and other micro-organisms;
bombesin;
vasoactive intestinal peptide;
neurotensin;
laminin fragments eg. YIGSR, PDSGR, IKVAV, LRE and KCQAGTFALRGDPQG,
N-formyl chemotactic peptides for targeting sites of leucocyte accumulation,
Platelet factor 4 (PF4) and fragments thereof,
RGD (Arg-Gly-Asp)-containing peptides, which may eg. target angiogenesis [R. Pasqualini et al., Nat Biotechnol. 1997 June; 15(6):542-6]; [E. Ruoslahti, Kidney Int. 1997 May;51(5):1413-7].
peptide fragments of $\alpha_2$-antiplasmin, fibronectin or beta-casein, fibrinogen or thrombospondin. The amino acid sequences of $\alpha_2$-antiplasmin, fibronectin, beta-casein, fibrinogen and thrombospondin can be found in the following references: $\alpha_2$-antiplasmin precursor [M. Tone et al., J. Biochem, 102, 1033, (1987)]; beta-casein [L. Hansson et al, Gene, 139, 193, (1994)]; fibronectin [A. Gutman et al, FEBS Lett., 207, 145, (1996)]; thrombospondin-1 precursor [V. Dixit et al, Proc. Natl. Acad. Sci., USA, 83, 5449, (1986)]; R. F. Doolittle, Ann. Rev. Biochem., 53, 195, (1984);

peptides which are substrates or inhibitors of angiotensin, such as: angiotensin II Asp-Arg-Val-Tyr-Ile-His-Pro-Phe (E. C. Jorgensen et al, *J. Med. Chem.*, 1979, Vol 22, 9, 1038-1044)

[Sar, Ile] Angiotensin II: Sar-Arg-Val-Tyr-Ile-His-Pro-Ile (R. K. Turker et al., *Science*, 1972, 177, 1203).

Angiotensin I: Asp-Arg-Val-Tyr-Ile-His-Pro-Phe-His-Leu.

Preferred BTM peptides are RGD peptides. A more preferred such RGD peptide comprises the fragment:

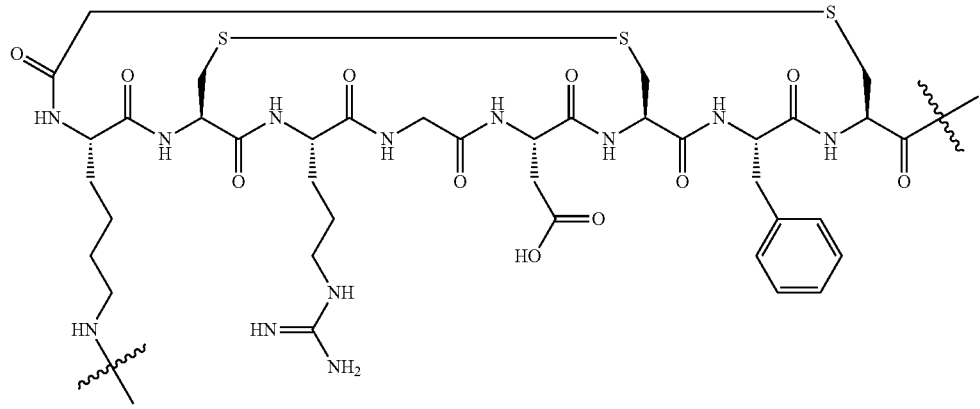 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

A most preferred such RGD peptide is when the BTM is a peptide of formula (A):

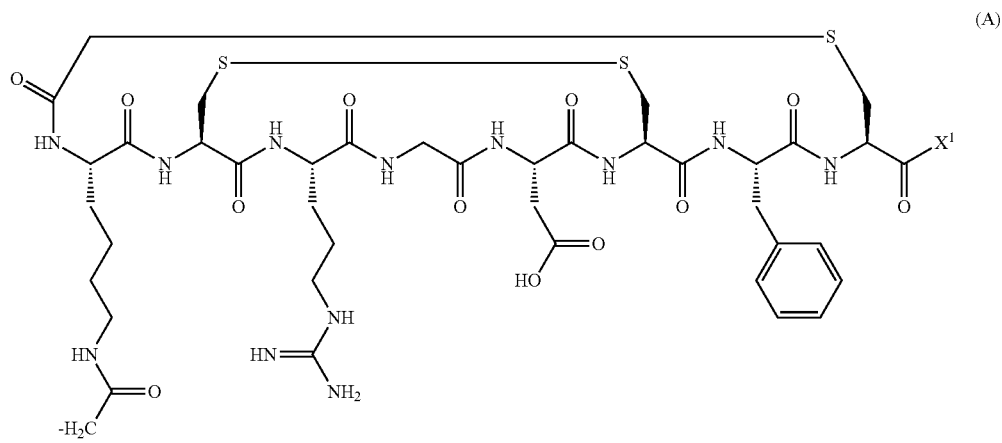

wherein $X^1$ is either —$NH_2$ or

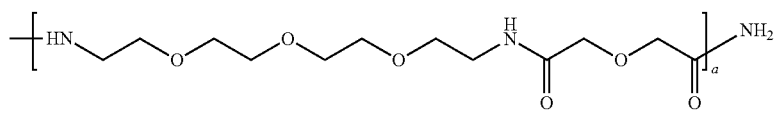

wherein a is an integer of from 1 to 10. In Formula A, a is preferably 1.

When the BTM is a peptide, one or both termini of the peptide, preferably both, have conjugated thereto a metabolism inhibiting group ($M^{IG}$). Having both peptide termini protected in this way is important for in vivo imaging applications, since otherwise rapid metabolism would be expected with consequent loss of selective binding affinity for the BTM peptide. By the term "metabolism inhibiting group" ($M^{IG}$) is meant a biocompatible group which inhibits or suppresses enzyme, especially peptidase such as carboxypeptidase, metabolism of the BTM peptide at either the amino terminus or carboxy terminus. Such groups are particularly important for in vivo applications, and are well known to those skilled in the art and are suitably chosen from, for the peptide amine terminus:

N-acylated groups —NH(C=O)$R^G$ where the acyl group —(C=O)$R^G$ has $R^G$ chosen from: $C_{1-6}$ alkyl, $C_{3-10}$ aryl groups or comprises a polyethyleneglycol (PEG) building block. Suitable PEG groups are described for the linker group ($L^1$), below. Preferred such PEG groups are the biomodifiers of Formulae Bio1 or Bio2 (below). Preferred such amino terminus $M^{IG}$ groups are acetyl, benzyloxycarbonyl or trifluoroacetyl, most preferably acetyl.

Suitable metabolism inhibiting groups for the peptide carboxyl terminus include: carboxamide, tert-butyl ester, benzyl ester, cyclohexyl ester, amino alcohol or a polyethyleneglycol (PEG) building block. A suitable $M^{IG}$ group for the carboxy terminal amino acid residue of the BTM peptide is where the terminal amine of the amino acid residue is N-alkylated with a $C_{1-4}$ alkyl group, preferably a methyl group. Preferred such $M^{IG}$ groups are carboxamide or PEG, most preferably such groups are carboxamide.

When the linker group (L) comprises a peptide chain of 1 to 10 amino acid residues, the amino acid residues are preferably chosen from glycine, lysine, arginine, aspartic acid, glutamic acid or serine. When L comprises a PEG moiety, it preferably comprises units derived from oligomerisation of the monodisperse PEG-like structures of Formulae Bio1 or Bio2:

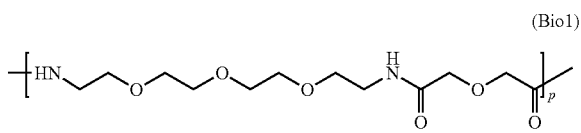

17-amino-5-oxo-6-aza-3,9,12,15-tetraoxaheptadecanoic acid of Formula Bio1 wherein p is an integer from 1 to 10. Alternatively, a PEG-like structure based on a propionic acid derivative of Formula Bio2 can be used:

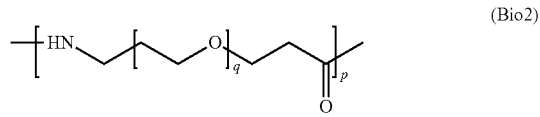

where p is as defined for Formula Bio1 and q is an integer from 3 to 15. In Formula Bio2, p is preferably 1 or 2, and q is preferably 5 to 12.

When the linker group does not comprise PEG or a peptide chain, preferred L groups have a backbone chain of linked atoms which make up the $-(A)_m$-moiety of 2 to 10 atoms, most preferably 2 to 5 atoms, with 2 or 3 atoms being especially preferred.

BTM peptides which are not commercially available can be synthesised by solid phase peptide synthesis as described in P. Lloyd-Williams, F. Albericio and E. Girald; *Chemical Approaches to the Synthesis of Peptides and Proteins*, CRC Press, 1997.

In a preferred embodiment, the agent of the first aspect is of Formula IA:

where, M, Q, and preferred aspects thereof are as defined for Formula I.

In the agent of Formulae I and IA, preferably at least one of $Y^1$ and $Y^2$ is $NR^1$, more preferably $Y^1=Y^2=NR^1$. In the agent of Formulae I and IA, x, y and z are each preferably 1. More preferably, x=y=z=1.

In the agent of Formulae I and IA, $R^1$ is preferably $-CH_3$ or $-CH_2C_6H_5$, more preferably $-CH_3$.

In a more preferred embodiment, the agent of the first aspect is of Formula IB:

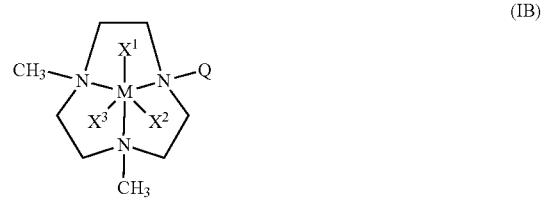

where, M, Q, and preferred aspects thereof are as defined for Formula I.

In Formulae I, IA and IB, $X^1$, $X^2$ and $X^3$ are preferably independently Cl, $^{19}F$ or $^{18}F$. More preferably, two of $X^1$, $X^2$ and $X^3$ are $^{19}F$, and the third is $^{18}F$.

In Formulae I, IA and IB, M is preferably $Al^{3+}$, $Ga^{3+}$, $In^{3+}$, $Sc^{3+}$ or $Y^{3+}$; more preferably $Ga^{3+}$, $In^{3+}$, $Sc^{3+}$ or $Y^{3+}$; most preferably $Ga^{3+}$ or $In^{3+}$; with $Ga^{3+}$ being the ideal.

Preferably, the imaging agent is provided in sterile form, i.e. in a form suitable for mammalian administration as is described in the fourth aspect (below).

The imaging agents of the first aspect can be obtained as described in the second aspect (below).

In a second aspect, the present invention provides a method of preparation of the agent of the first aspect, which comprises reaction of a precursor of Formula II with a supply of $[^{18}F]$-fluoride or $[^{18}F]NaF$, optionally in the presence of $[^{19}F]$-fluoride, in a suitable solvent:

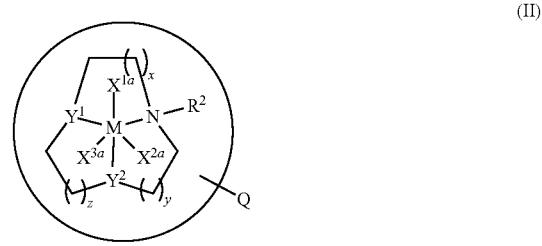

where M, $Y^1$, $Y^2$, Q, x, y and z and preferred embodiments thereof are as defined for Formulae I, IA and IB of the first aspect, and $X^{1a}$, $X^{2a}$ and $X^{3a}$ are independently Br or Cl. As with Formula I, Q may be present or absent in Formula II. When Q is absent in Formula II, $R^2$ is an $R^1$ group.

The $[^{18}F]$-fluoride may either be:
I) delivered directly from a cyclotron and formulated using an ion exchange cartridge and appropriate eluent; or
II) in the form of GMP $[^{18}F]NaF$ produced on an automated platform in a GMP facility.

The production of $[^{18}F]$-fluoride suitable for radiopharmaceutical applications is well-known in the art, and has been reviewed by Hjelstuen et at [Eur. J. Pharm. Biopharm., 78(3), 307-313 (2011)], and Jacobson et at [Curr. Top. Med. Chem., 10(11), 1048-1059 (2010)]. $[^{18}F]NaF$ can be produced using an "automated synthesizer" as described in the fifth aspect (below).

The "suitable solvent" include: acetonitrile, a $C_{1-4}$ alkylalcohol, dimethylformamide, tetrahydrofuran, or dimethylsulfoxide, or aqueous mixtures of any thereof, or water.

Aqueous buffers can be used in the pH range of 4-8, more preferably 5-7. A preferred solvent is aqueous in nature, and is more preferably a biocompatible carrier solvent as defined in the fourth aspect (below).

The $^{19}$F-carrier (when used) may be in the form of:
I) alkaline metal salt (eg NaF, KF, CsF etc); or
II) in the presence of "non-metallic counter ions" (eg [R$_4$N]F where R=alkyl), [Ar$_4$P]F; [Ar$_3$S]F
III) metal cryptand counterions eg [K(kryptofix 2.2.2)]F, [Na(kryptofix 2.2.2)]F, [N(18-crown-6)]F etc.

In the precursor of Formula II, Q is preferably present. In order to prepare the preferred agents of Formula IA and IB, precursors of Formula IIA and IIB respectively are used:

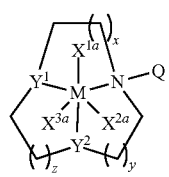

(IIA)

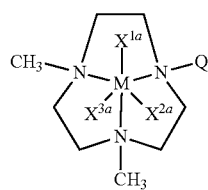

(IIB)

For the precursor of Formulae II, IIA, or IIB, it is preferred that $X^{1a}=X^{2a}=X^{3a}=Cl$.

The precursor used in the second aspect is non-radioactive. Preferably, the precursor is provided in sterile form, to facilitate the preparation of imaging agents in pharmaceutical composition form—as is described in the fourth aspect (below).

When Q is absent, the precursor of the second aspect can be obtained by conventional metal coordination chemistry—using analogous metal complexation conditions to those described for the bifunctional chelate approach.

When Q is present, the precursor of the second aspect can be obtained by the bifunctional chelate approach. The term "bifunctional chelate" has its conventional meaning, and refers to a chelating agent having covalently attached thereto a pendant functional group. The functional group is used as a reactive site to attach the chelator to the BTM. The bifunctional chelate approach and associated syntheses have been described by Bartholoma et at [Chem. Rev., 110(5), 2903-2920 (2010)]; Chakraborty et at [Curr. Top. Med. Chem., 10(11), 1113-1134 (2010)] and Brechbiel et at [Quart. J. Nucl. Med. Mol. Imaging, 52(2), 166-173 (2008)]. The functional group of the present invention is preferably an amine, carboxylic acid or activated ester, more preferably a primary amine or an activated ester. Bifunctional chelators having a pendant amine functional group can be conjugated to the carboxyl group of a BTM. Bifunctional chelators having a carboxyl or activated ester functional group can be conjugated to an amine group of a BTM.

By the term "activated ester" or "active ester" is meant an ester derivative of the associated carboxylic acid which is designed to be a better leaving group, and hence permit more facile reaction with nucleophile, such as amines. Examples of suitable active esters are: N-hydroxysuccinimide (NHS); sulfo-succinimidyl ester; pentafluorophenol; pentafluorothiophenol; para-nitrophenol; hydroxybenzotriazole and PyBOP (i.e. benzotriazol-1-yl-oxytripyrrolidinophosphonium hexafluorophosphate). Preferred active esters are N-hydroxysuccinimide or pentafluorophenol esters, especially N-hydroxysuccinimide esters.

When a bifunctional chelator having a carboxyl functional group is conjugated to an amine group of a BTM, an activating agent is used. By the term "activating agent" is meant a reagent used to facilitate coupling between an amine and a carboxylic acid to generate an amide. Suitable such activating agents are known in the art and include carbodiimides such as EDC [N-(3-dimethylaminopropyl)-N'-ethylcarbodiimide and N,N'-dialkylcarbodiimides such as dicyclohexylcarbodiimide or diisopropylcarbodiimide; and triazoles such as HBTU [O-(benzotriazol-1-yl)-N,N,N', N'-tetramethyluronium hexafluorophosphate], HATU [O-(7-azabenzotriazol-1-yl)-N,N,N',N'-tetramethyluronium hexafluorophosphate], and PyBOP [benzotriazol-1-yloxy)tripyrrolidinophosphonium hexafluorophosphate]. Such activating agents are commercially available. Further details are given in March's Advanced Organic Chemistry, 5$^{th}$ Edition, pages 508-510, Wiley Interscience (2001). A preferred such activating agent is EDC.

A preferred method of preparation of the precursor of Formula II is via metal complex formation with a chelator or chelator-BTM conjugate of Formula III, wherein Q may be present or absent:

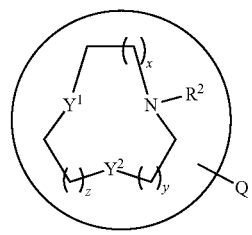

(III)

wherein Y', Y$^2$, Q$^3$, x, y and z and preferred embodiments thereof are as described in the first aspect (above).

In Formula III, Q is preferably present with preferred embodiments of Q as described in the first aspect (above).

The chelators and chelator conjugates of Formula III can be prepared by literature methods. Sakamoto et at [J. Org. Chem., 51, 4974 (1986)] disclose the synthesis of such chelators having an NO$_2$ donor set. Chelators of Formula III having an N$_2$O donor set, such as 1,4-diaza-7-oxa-cyclononane, are described by Hancock et at [J. Am. Chem. Soc., 104, 291-292 (1982)], and Sessler et at [Tetrahedron, 49(39), 8727-8738 (1993)].

Larger ring size N3 donor macrocycles (and their N-methyl derivatives) are described in Macrocycle Synthesis a Practical Approach, Ed. D. Parker, OUP, 1996, p 20 and references therein.

A preferred chelator-BTM conjugate within Formula III is of Formula IIIA:

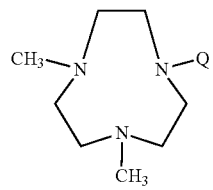

(IIIA)

The chelator-BTM conjugate of Formula IIIA can be prepared using analogous chemistry to McBride et at [Bioconj. Chem., 21(7), 1331-1340 (2010); Bioconj. Chem., 22, 1793-1803 (2011) and Appl. Rad. Isot., 70, 200-204 (2012)], e.g:

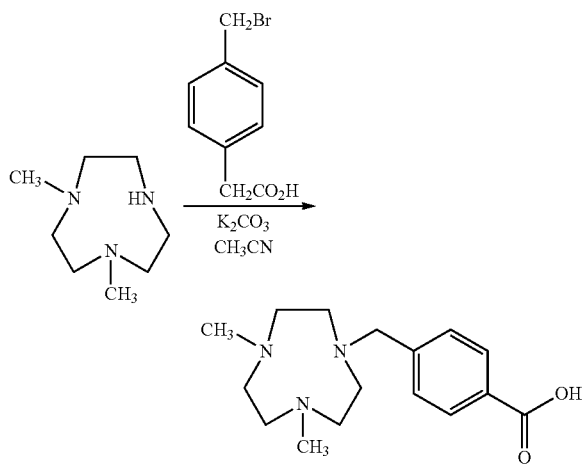

The starting material 1,4-dimethyl-tacn can be obtained by the method of Wieghardt et at [Inorg. Synth., 32, 75-81 (1998); Z. Anorg. Allg. Chem., 608, 60-68 (1992)]. Tacn and Me$_3$-tacn are commercially available. Me$_3$-tacn can also be obtained by the method of Wieghardt et at [Inorg Chem., 21, 3086 (1982)]. N-functionalised tacn chelators can be obtained by the method of Martin et at [J. Org. Chem., 47, 412 (1982)] or Mahapatra et at [J. Am. Chem. Soc., 118, 11555 (1996)]. Backbone-functionalised tacn chelators are described by Kuppers et at [Inorg. Chem., 25, 2400 (1986)].

In a third aspect, the present invention provides a precursor of Formula HA or JIB as defined in the second aspect, where Q comprises a BTM which is chosen from: a 3-100 mer peptide, an enzyme substrate, an enzyme antagonist an enzyme agonist, an enzyme inhibitor or a receptor-binding compound.

Preferred aspects of the precursor of Formula IIA or JIB in the third aspect are as described in the second aspect of the invention (above). Preferred aspects of the Q group and BTM in the third aspect are as described in the first aspect of the invention (above).

The precursor of the third aspect is preferably "in a form suitable for mammalian administration" as defined below, most preferably in lyophilized form.

In a fourth aspect, the present invention provides a radiopharmaceutical composition which comprises the imaging agent of the first aspect, together with a biocompatible carrier, in a form suitable for mammalian administration.

Preferred aspects of the imaging agent in the fourth aspect are as described in the first aspect of the present invention (above).

By the phrase "in a form suitable for mammalian administration" is meant a composition which is sterile, pyrogen-free, lacks compounds which produce toxic or adverse effects, and is formulated at a biocompatible pH (approximately pH 4.0 to 10.5). Such compositions lack particulates which could risk causing emboli in vivo, and are formulated so that precipitation does not occur on contact with biological fluids (e.g. blood). Such compositions also contain only biologically compatible excipients, and are preferably isotonic.

The "biocompatible carrier" is a fluid, especially a liquid, in which the imaging agent can be suspended or preferably dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous buffer solution comprising a biocompatible buffering agent (e.g. phosphate buffer); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). Preferably the biocompatible carrier is pyrogen-free water for injection, isotonic saline or phosphate buffer.

The imaging agents and biocompatible carrier are each supplied in suitable vials or vessels which comprise a sealed container which permits maintenance of sterile integrity and/or radioactive safety, plus optionally an inert headspace gas (eg. nitrogen or argon), whilst permitting addition and withdrawal of solutions by syringe or cannula. A preferred such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (eg. to change the headspace gas or degas solutions), and withstand pressure changes such as reductions in pressure without permitting ingress of external atmospheric gases, such as oxygen or water vapour.

Preferred multiple dose containers comprise a single bulk vial which contains multiple patient doses, whereby single patient doses can thus be withdrawn into clinical grade syringes at various time intervals during the viable lifetime of the preparation to suit the clinical situation. Pre-filled syringes are designed to contain a single human dose, or "unit dose" and are therefore preferably a disposable or other syringe suitable for clinical use. The pharmaceutical compositions of the present invention preferably have a dosage suitable for a single patient and are provided in a suitable syringe or container, as described above.

The pharmaceutical composition may contain additional optional excipients such as: an antimicrobial preservative, pH-adjusting agent, filler, radioprotectant, solubiliser or osmolality adjusting agent. By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (i.e. 4-aminobenzoic acid), gentisic acid (i.e. 2,5-dihydroxybenzoic acid) and salts thereof with a biocompatible cation as described above. By the term "solubiliser" is meant an additive present in the composition which increases the solubility of the imaging agent in the solvent. A preferred such solvent is aqueous media, and hence the solubiliser preferably improves solubility in water. Suitable such solubilisers include: $C_{1-4}$ alcohols; glycerine; polyethylene glycol (PEG); propylene glycol; polyoxyethylene sorbitan monooleate; sorbitan monooloeate; polysorbates; poly(oxyethylene)poly(oxypropylene)poly(oxyethylene) block copolymers (Pluronics™); cyclodextrins (e.g.

alpha, beta or gamma cyclodextrin, hydroxypropyl-β-cyclodextrin or hydroxypropyl-γ-cyclodextrin) and lecithin.

By the term "antimicrobial preservative" is meant an agent which inhibits the growth of potentially harmful micro-organisms such as bacteria, yeasts or moulds. The antimicrobial preservative may also exhibit some bactericidal properties, depending on the dosage employed. The main role of the antimicrobial preservative(s) of the present invention is to inhibit the growth of any such micro-organism in the pharmaceutical composition. The antimicrobial preservative may, however, also optionally be used to inhibit the growth of potentially harmful micro-organisms in one or more components of kits used to prepare said composition prior to administration. Suitable antimicrobial preservative(s) include: the parabens, i.e. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the composition is within acceptable limits (approximately pH 4.0 to 10.5) for human or mammalian administration. Suitable such pH-adjusting agents include pharmaceutically acceptable buffers, such as tricine, phosphate or TRIS [i.e. tris(hydroxymethyl)aminomethane], and pharmaceutically acceptable bases such as sodium carbonate, sodium bicarbonate or mixtures thereof.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

The radiopharmaceutical compositions of the fourth aspect may be prepared under aseptic manufacture (i.e. clean room) conditions to give the desired sterile, non-pyrogenic product. It is preferred that the key components, especially the associated reagents plus those parts of the apparatus which come into contact with the imaging agent (e.g. vials) are sterile. The components and reagents can be sterilised by methods known in the art, including: sterile filtration, terminal sterilisation using e.g. gamma-irradiation, autoclaving, dry heat or chemical treatment (e.g. with ethylene oxide). It is preferred to sterilise some components in advance, so that the minimum number of manipulations needs to be carried out. As a precaution, however, it is preferred to include at least a sterile filtration step as the final step in the preparation of the pharmaceutical composition.

The radiopharmaceutical compositions of the present invention may be prepared by various methods:
  (i) aseptic manufacture techniques in which the $^{18}$F-radiolabelling step is carried out in a clean room environment;
  (ii) terminal sterilisation, in which the $^{18}$F-radiolabelling is carried out without using aseptic manufacture and then sterilised at the last step [e.g. by gamma irradiation, autoclaving dry heat or chemical treatment (e.g. with ethylene oxide)];
  (iii) aseptic manufacture techniques in which the $^{18}$F-radiolabelling step is carried out using an automated synthesizer apparatus.

Method (iii) is preferred, and is described more fully in the fifth aspect (below).

In a fifth aspect, the present invention provides a method of preparation of the radiopharmaceutical composition of the fourth aspect, which comprises carrying out the method of preparation of the third aspect using an automated synthesizer apparatus.

Preferred aspects of the imaging agent, precursor and composition in the fifth aspect are as described in the first, third and fourth aspects of the present invention respectively.

By the term "automated synthesizer" is meant an automated module based on the principle of unit operations as described by Satyamurthy et at [Clin. Positr. Imag., 2(5), 233-253 (1999)]. The term 'unit operations' means that complex processes are reduced to a series of simple operations or reactions, which can be applied to a range of materials. Such automated synthesizers are preferred for the method of the present invention especially when a radiopharmaceutical composition is desired. They are commercially available from a range of suppliers [Satyamurthy et al, above], including: GE Healthcare; CTI Inc; Ion Beam Applications S.A. (Chemin du Cyclotron 3, B-1348 Louvain-La-Neuve, Belgium); Raytest (Germany) and Bioscan (USA).

Commercial automated synthesizers also provide suitable containers for the liquid radioactive waste generated as a result of the radiopharmaceutical preparation. Automated synthesizers are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours. The automated synthesizer preferably comprises a cassette. By the term "cassette" is meant a piece of apparatus designed to fit removably and interchangeably onto an automated synthesizer apparatus (as defined above), in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

The cassette is versatile, typically having several positions where reagents can be attached, and several suitable for attachment of syringe vials of reagents or chromatography cartridges (e.g. solid phase extraction or SPE). The cassette always comprises a reaction vessel. Such reaction vessels are preferably 1 to 10 cm$^3$, most preferably 2 to 5 cm$^3$ in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes are designed to be suitable for radiopharmaceutical manufacture and are therefore manufactured from materials which are of pharmaceutical grade and ideally also are resistant to radiolysis.

Preferred automated synthesizers of the present invention comprise a disposable or single use cassette which comprises all the reagents, reaction vessels and apparatus necessary to carry out the preparation of a given batch of radiofluorinated radiopharmaceutical. The cassette means that the automated synthesizer has the flexibility to be capable of making a variety of different radiopharmaceuticals with minimal risk of cross-contamination, by simply changing the cassette. The cassette approach also has the advantages of: simplified set-up hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

Included in this aspect of the invention, is the use of an automated synthesizer apparatus to prepare the radiopharmaceutical composition of the second aspect.

Included in this aspect of the invention, is the use of a suitable cassette in conjunction with an automated synthesizer apparatus to prepare the radiopharmaceutical composition of the second aspect.

In a sixth aspect, the present invention provides a method of the preparation of the radiopharmaceutical composition of the fourth aspect, which comprises carrying out the method of the third aspect, wherein the precursor is provided in sterile, lyophilized form.

Preferred aspects of the imaging agent, precursor and composition in the sixth aspect are as described in the first, third and fourth aspects of the present invention respectively. The lyophilized precursor of the sixth aspect is preferably provided as a non-radioactive kit in a pharmaceutical grade container, preferably a septum-sealed vial, as is described in the fourth aspect (above).

In a seventh aspect, the present invention provides a method of imaging the human or animal body which comprises generating an image of at least a part of said body to which the imaging agent of the first aspect, or the composition of the fourth aspect has distributed using PET, wherein said imaging agent or composition has been previously administered to said body.

Preferred aspects of the imaging agent or composition in the seventh aspect are as described in the first and fourth aspects respectively of the present invention (above).

The invention is illustrated by the non-limiting Examples detailed below. All reactions were operated under a nitrogen atmosphere with standard Schlenk glassware, vacuum or Glove box techniques unless otherwise noted. The solvents were dried and degassed by refluxing over standard drying agents and distilled immediately prior to use. Tacn and Me$_3$-tacn are commercially available, eg. from Aldrich. BzMe$_2$-tacn was obtained by the method of Spiccia et at [Inorg. Chem., 45(9), 3746-3755 (2006)]. All other chemicals were obtained from commercial sources.

Examples 1, 2, 4 and 5 provide the syntheses of aluminium complexes of the invention. Examples 6 to 7 and 9, 11, 12 and 14 provide the syntheses of gallium and indium complexes respectively of the invention. Example 3 demonstrates the fluoride exchange of an aluminium complex of the invention, showing that the exchange occurs under mild conditions with aqueous KF and leads to a stable, isolable product. Examples 8 and 10 provide similar evidence for gallium complexes of the invention with different sources of fluoride. Examples 13 and 15 provide similar evidence for the indium complexes of this invention. The higher affinities of fluoride for Ga(III) relative to Al(III) means the formation of [GaF$_3$(Me$_3$-tacn)] from the corresponding tri-chloride derivative (using NMe$_4$F or NBu$_4$F) is rapid and clean in MeCN solution. In contrast, the [AlF$_3$(Me$_3$-tacn)] was not formed by an analogous exchange reaction in neat MeCN, but is formed at room temperature when aqueous KF is added to a MeCN solution of [AlCl$_3$(Me$_3$-tacn)].

$^{19}$F and $^{71}$Ga NMR studies show complete conversion to [GaF$_3$(Me$_3$-tacn)]. Furthermore they confirm that the structure of the complex is retained in solution. The resulting [GaF$_3$(Me$_3$-tacn)] complex is considerably more stable than the chloride and bromide analogues, and resistant to hydrolysis in aqueous solution. The structure has also been confirmed crystallographically (FIG. 2). This provides clear evidence that direct incorporation of fluoride into the coordination sphere of carefully selected metal ions is entirely feasible, as well as establishing the high stability of the resulting fluoro complexes, even in aqueous solution. NMR data is summarised in Table 1.

Example 16 provides $^8$F radiolabelling of a metal complex of the invention.

Chelators of the Invention

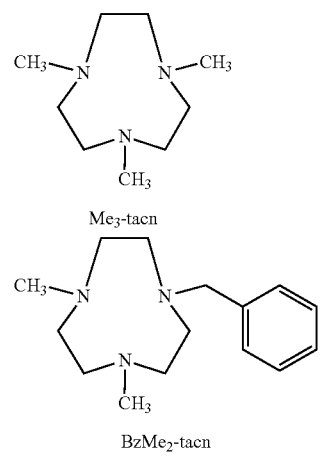

Me$_3$-tacn

BzMe$_2$-tacn

ABBREVIATIONS

Boc: tert-Butyloxycarbonyl.
BzMe$_2$tacn: 1,4,-dimethyl-7-benzyl-1,4,7-triazacyclononane.
DMF: dimethylformamide
DMSO: Dimethylsulfoxide.
GMP: Good Manufacturing Practice.
HPLC: High performance liquid chromatography.
MeCN: acetonitrile.
Me$_3$tacn: 1,4,7-trimethyl-1,4,7-triazacyclononane.
SPE: solid phase extraction.
Tacn: 1,4,7-triazacyclononane
THF: tetrahydrofuran.
tBu: tert-Butyl.

DESCRIPTION OF THE FIGURES

FIGS. 1 to 3 show the X-ray crystal structures of metal complexes of the invention.

EXAMPLE 1

Synthesis of [AlCl$_3$(Me-tacn)]

AlCl$_3$ (0.067 g, 0.50 mmol) was added to a solution of Me$_3$-tacn (0.086 g, 0.50 mmol) in CH$_3$CN (5 mL) at room temperature with stirring leading to rapid formation of a precipitate. After 30 mins. the solvent was removed by filtration. The white precipitate was washed with small amount of $CH_2Cl_2$ solvent and dried in vacuo. Yield: 0.11 g, 72%. Colorless crystals were obtained by cooling the $CH_3CN$ solution in the fridge for several days. The crystals were washed with $CH_2Cl_2$.

Anal. Calc. for $C_9H_{21}AlCl_3N_3$. 0.2 $CH_2Cl_2$: C, 34.4; H, 6.7; N, 13.1. Found: C, 34.2; H, 7.2; N, 13.9.

$^1$H NMR ($CD_2Cl_2$, 298 K): δ 3.23 (m, [6H], $CH_2$), 2.86 (s, [9H], $CH_3$), 2.67 (m, [6H], $CH_2$).

IR (Nujol, v/cm$^{-1}$): 389, 375 (Al—Cl).

An X-ray crystal structure was obtained, see FIG. 1.

EXAMPLE 2

Synthesis of [AlBr$_3$(Me$_3$-tacn)]

Al Br$_3$ (0.133 g, 0.50 mmol) was added to a solution of Me$_3$-tacn (0.086 g, 0.50 mmol) in $CH_2Cl_2$ (5 mL) at room temperature with stirring which leads a formation of precipitate. After 30 mins. the solvent was removed by filtration. The white precipitate was washed with small amount of $CH_2Cl_2$ solvent and dried in vacuo. Yield: 0.16 g, 74%.

Anal. Calc. for $C_9H_{21}Al Br_3N_3$: C, 24.7; H, 4.8; N, 9.6. Found: C, 24.6; H, 5.3; N, 8.9.

$^1$H NMR ($CD_2Cl_2$, 297 K): δ 3.43 (m, [6H], $CH_2$), 2.98 (m, [9H], $CH_3$), 2.73 (m, [6H], $CH_2$).

IR (Nujol, v/cm$^{-1}$): 324 (Al—Br).

EXAMPLE 3

Synthesis of [AlF$_3$(Me$_3$-tacn)]·xH$_2$O

Method 1

AlF$_3$. 3 H$_2$O (0.100 g, 0.73 mmol) was suspended in freshly distilled water (7 mL). Me$_3$-tacn (0.125 g, 0.73 mmol) was then added and the pale yellow suspension was transferred into a Teflon container and loaded into a stainless steel high pressure vessel (Parr instrument company, part no 276AC-T304-04 1 101) and heated to 180° C. for 15 h. The vessel was then allowed to cool. A dark yellow-brown solution had formed. A small aliquot of the reaction solution was retained to grow crystals. For the remaining reaction mixture the volatiles were removed in vacuo, giving a light brown solid which was washed with hexane and filtered. The resulting white solid was dried in vacuo. Yield: 0.12 g, 53%.

Anal. Calc. for $C_9H_{21}Al F_3N_3$. 3H$_2$O: C, 34.9; H, 8.8; N, 13.6. Found: C, 34.3; H, 8.9; N, 14.7%.

$^1$H NMR (CD$_3$CN, 298 K): δ 2.84-2.76 (m, [6H], $CH_2$), 2.72-2.65 (m, [6H], $CH_2$), 2.55 (s, [9H], $CH_3$), 2.19 (s, H$_2$O).

IR (Nujol, v/cm$^{-1}$): 3438 br (H$_2$O), 1668 (H$_2$O), 633, 614 (Al—F).

Slow evaporation of the reaction solvent gave crystals suitable for X-ray diffraction.

Method 2

A solution of KF (0.058 g, 0.99 mmol) in water (2 mL) was added to a suspension of [AlCl$_3$(Me$_3$-tacn)] (Example 1, 0.100 g, 0.33 mmol) in MeCN (5 mL) at room temperature. A white precipitate formed initially which redissolved into solution after a few minutes. NMR spectroscopic data on the solution were as for Method 1.

EXAMPLE 4

Synthesis of [AlCl$_3$(BzMe$_2$-tacn)]

AlCl$_3$ (0.067 g, 0.50 mmol) was added to a solution of BzMe$_2$-tacn (0.13 g, 0.50 mmol) in $CH_3CN$ (2 mL) at room temperature with stirring which led to the formation of precipitate. After 30 min the solvent was removed by filtration. The white precipitate was washed with small amount of $CH_2Cl_2$ solvent and dried in vacuo. Yield: 0.13 g, 68%.

Anal. Calc. for $C_{15}H_{25}AlCl_3N_3$: C, 47.3; H, 6.6; N, 11.0. Found: C, 47.0; H, 6.6; N, 11.2.

$^1$H NMR ($CD_2Cl_2$, 298 K): δ 7.31 (m, [5H], ArH), 4.58 (s, [2H], Ar—$CH_2$), 3.54 (m, [2H], tacn-$CH_2$), 3.29 (m, [4H], tacn-$CH_2$), 2.92 (s, [6H], $CH_3$), 2.65 (m, [4H], tacn-$CH_2$), 2.28 (m, [2H], tacn-$CH_2$).

IR (Nujol, v/cm$^{-1}$): 398, 385 (Al—Cl).

EXAMPLE 5

Synthesis of [Albr$_3$(BzMe$_2$-tacn)]

Al Br$_3$ (0.133 g, 0.50 mmol) was added to a solution of BzMe$_2$-tacn (0.13 g, 0.50 mmol) in $CH_2Cl_2$ (2 mL) at room temperature with stirring which immediately precipitated a white solid. After 30 min the solvent was removed by filtration. The white precipitate was washed with small amount of $CH_2Cl_2$ solvent and dried in vacuo. Yield: 0.19 g, 74%.

$^1$H NMR ($CD_2Cl_2$, 298 K): δ 7.31 (m, [5H], ArH), 4.75 (m, [2H], Ar—$CH_2$), 3.72 (m, [2H], tacn-$CH_2$), 3.46 (m, [4H], tacn-$CH_2$), 3.04 (m, [6H], $CH_3$), 2.70 (m, [4H], tacn-$CH_2$), 2.33 (m, [2H], tacn-$CH_2$).

IR (Nujol, v/cm$^{-1}$): 343, 325 sh (Al—Br).

EXAMPLE 6

Synthesis of [GaCl$_3$(Me$_3$-tacn)]

Me$_3$-tacn (0.09 g, 0.52 mmol) was added to a solution of GaCl$_3$ (0.088 g, 0.50 mmol) in anhydrous $CH_2Cl_2$ (8 mL) at room temperature with stirring. After ca. 30 mins, a white precipitate started to appear. After 2 h stirring was stopped and the mixture was concentrated to afford more precipitate, the white powdered product was filtered from the solution and dried in vacuo. Yield: 0.110 g, 60%.

Anal. Calc. for $C_9H_{21}Cl_3GaN_3$: C, 31.1; H, 6.1; N, 12.1. Found C, 31.2; H, 5.9; N, 12.1%.

$^1$H NMR ($CD_2Cl_2$, 298 K): δ 3.2 (br m, [6H], $CH_2$), 2.85 (br s, [9H], Me), 2.6 (br m, [6H], $CH_2$).

IR (Nujol, v/cm$^{-1}$): 290, 275 (Ga—Cl).

An X-ray crystal structure was determined, see FIG. 2.

EXAMPLE 7

Synthesis of [GaF$_3$(Me$_3$-tacn)]

Method as for [GaCl$_3$(Me$_3$-tacn)] (Example 6) but using Me$_3$-tacn (0.086 g, 0.50 mmol) and GaBr$_3$ (0.150 g, 0.50 mmol). White solid. Yield: 0.106 g, 45%.

Anal. Calc. for $C_9H_{21}Br_3GaN_3$: C, 22.5; H, 4.4; N, 8.7. Found C, 22.4; H, 4.6; N, 8.6%.

$^1$H NMR ($CD_2Cl_2$, 298 K): δ 3.3 (br m, [6H], $CH_2$), 2.9 (br s, [9H], Me), 2.7 (br m, [6H], $CH_2$).

Required for $C_9H_{21}Br_3GaN_3$: C, 22.49; H, 4.40; N, 8.74. Found C, 22.41; H, 4.62; N, 8.56%

EXAMPLE 8

Synthesis of [GaF$_3$(Me$_3$-tacn)].4H$_2$O

Method 1:

[GaCl$_3$(Me$_3$-tacn)] (Example 6, 0.1 g, 0.28 mmol) was added to CH$_2$Cl$_2$ (8 mL) and stirred for ca. 15 mins., the solid mostly dissolved to give a clear solution. [NBu$_4$]F in THF (1 mol dm$^{-3}$, 0.84 mL, 0.84 mmol) was added to the mixture via syringe and the reaction was stirred for ca. 10 mins., giving a clear, colorless solution. The solution was filtered and the filtrate was taken to dryness in vacuo. The resulting colorless solid was re-dissolved in CH$_2$Cl$_2$, the solution was filtered and the CH$_2$Cl$_2$ was left to evaporate, giving a colorless solid product. Yield: 50%.

Anal. Calc. for C$_9$H$_{21}$F$_3$GaN$_3$. 3 H$_2$O: C, 30.7; H, 7.7; N, 11.9. Found: C, 30.6; H, 6.9; N, 11.0%.

$^1$H NMR (CD$_2$Cl$_2$, 298 K): δ 2.85-2.94 (br m, [6H], CH$_2$), 2.67 (s, [9H], Me), 2.55-2.61 (br m, [6H], CH$_2$, 2.17 (s, H$_2$O).

IR (Nujol, v/cm$^{-1}$): 3481, 3429 (H$_2$O), 1648 (H$_2$O), 530, 492 (Ga—F).

Method 2:

[GaCl$_3$(Me$_3$-tacn)] (Example 6, 0.05 g, 0.15 mmol) was suspended in 5 mL anhydrous CH$_2$Cl$_2$. The suspension was treated with [NMe$_4$]F (0.042 g, 0.45 mmol) and stirred at room temperature for 1 h. The [NMe$_4$]Cl by-product was removed by filtration. The resulting colorless filtrate was treated with 5 mL hexane, resulting in a white precipitate which was isolated by filtration and dried in vacuo. Yield: 0.037 g, 74%.

Spectroscopic data as for Method 1.

Method 3:

[GaCl$_3$(Me$_3$-tacn] (Example 6, 0.05 g, 0.15 mmol) was suspended in anhydrous MeCN (5 mL). A solution of KF (0.026 g, 0.45 mmol) in water (2 mL) was added drop-wise, leading to rapid dissolution and forming a colorless solution. The mixture was stirred for a further 1 h at room temperature.

Spectroscopic data as for Method 1.

Colourless crystals were grown from the CH$_2$Cl$_2$ solution of the product upon slow evaporation. An X-ray crystal structure was obtained, see FIG. 2.

EXAMPLE 9

Synthesis of [GaCl$_3$(BzMe$_2$-tacn)]

BzMe$_2$-tacn (0.125 g, 0.50 mmol) was added to a solution of GaCl$_3$ (0.088 g, 0.50 mmol), 1:1, in dry CH$_2$Cl$_2$ (5-8 mL) at room temperature and stirred. After approximately 30 min. small quantities of a white precipitate started to form. After 12 hours, stirring was stopped and the mixture was concentrated by removal of CH$_2$Cl$_2$, which caused further precipitation of the product. The white product was filtered from the yellowish solution under nitrogen. The white powdered product was dried under vacuum for 2 h. Yield: 0.089 g, 42%.

Anal. Calc. for C$_{15}$H$_{25}$Cl$_3$GaN$_3$: C, 42.5; H, 6.0; N, 9.9. Found C, 42.2; H, 6.0; N, 9.6%.

$^1$H NMR (CD$_2$Cl$_2$, 298 K): δ 7.30 (br m, [5H], ArH), 4.71 (s, [2H], Ar—CH$_2$), 3.67 (br, [$^2$H], tacn-CH$_2$), 3.20 (br, [2H], tacn-CH$_2$), 2.92 (br s, [6H], CH$_3$), 2.75 (br m, [2H], tacn-CH$_2$), 2.62 (br m, [2H], tacn-CH$_2$), 2.40 (br m, [2H], CH$_2$).

IR (Nujol, v/cm$^{-1}$): 301, 280 (Ga—Cl).

EXAMPLE 10

Synthesis of [GaF$_3$(BzMe$_2$-tacn)].xH$_2$O

[GaCl$_3$(BzMe$_2$-tacn)] (Example 9, 0.05 g, 0.10 mmol) was suspended in 5 mL anhydrous CH$_2$Cl$_2$. The suspension was treated with [NMe$_4$]F (0.03 g, 0.30 mmol) and stirred at room temperature for 1 h. The [NMe$_4$]Cl by-product was removed by filtration. The resulting colorless filtrate was treated with 5 mL anhydrous hexane, forming a white precipitate which was isolated by filtration and dried in vacuo. Yield: 0.035 g, 80%.

$^1$H NMR (D$_2$O, 298 K): δ 7.30 (m, [5H], ArH), 4.73 (s, [2H], Ar—CH$_2$), 3.17 (m, [4H], tacn-CH$_2$), 2.88 (m, [4H], tacn-CH$_2$), 2.73 (s, [6H], CH$_3$), 2.36 (m, [4H], tacn-CH$_2$), 2.25 (s, H$_2$O).

IR (Nujol, v/cm$^{-1}$): 3390, 1654 (H$_2$O) 526, 515 (Ga—F).

EXAMPLE 11

Synthesis of [InCl$_3$(Me$_3$-tacn)]

Me$_3$-tacn (0.086 g, 0.50 mmol) was added to a solution of InCl$_3$ (0.110 g, 0.50 mmol), 1:1, and dry CH$_2$Cl$_2$ (5-8 mL) at room temperature and stirred. After approximately 30 min. a white precipitate started to form. After 2 hours, stirring was stopped and the mixture was concentrated which caused further precipitation of the product. The white product was filtered from solution under nitrogen and was dried under vacuum for 2 h. Yield: 0.113 g, 57%.

Anal. Calc. for C$_9$H$_{21}$Cl$_3$InN$_3$: C, 27.5; H, 5.4; N, 10.7. Found C, 27.8; H, 5.4; N, 10.9%.

$^1$H NMR (CDCl$_3$, 298 K): δ 3.1 (br m, [6H], CH$_2$), 2.8 (br m, [15H], Me and CH$_2$).

IR (Nujol, v/cm$^{-1}$): 287, 269 (In—Cl).

EXAMPLE 12

Synthesis of [InBr$_3$(Me$_3$-tacn)]

Me$_3$-tacn (0.087 g, 0.50 mmol) was added to a solution of InBr$_3$ (0.177 g, 0.50 mmol), 1:1, in dry CH$_2$Cl$_2$ (5-8 mL) at room temperature and stirred. After approximately 30 minutes a white precipitate had started to form. After 2 h, stirring was stopped and the mixture was concentrated by removal of CH$_2$Cl$_2$, which caused further precipitation of the product. The solid product was filtered from the colourless filtrate under nitrogen and dried under vacuum for 2 h. Yield: 0.162 g, 68%.

Anal. Calc. for C$_9$H$_{21}$Br$_3$InN$_3$: C, 20.5; H, 4.0; N, 8.0. Found C, 19.8; H, 4.0; N, 7.4%.

$^1$H NMR (CD$_2$Cl$_2$, 298 K): δ 3.18 (br m, [6H], CH$_2$), 2.78 (br s, [9H], Me), 2.67 (br m, [6H], CH$_2$).

EXAMPLE 13

Synthesis of [InF$_3$(Me$_3$-tacn)].H$_2$O

Method 1:

[InCl$_3$(Me$_3$-tacn)] (Example 11, 0.214 g, 0.54 mmol) was added to CH$_2$Cl$_2$ (8 mL) and stirred for ca. 15 mins., this gave a cloudy suspension. [N"Bu$_4$]F in THF (1 mol dm$^{-3}$, 1.63 mL, 1.63 mmol) was added to the mixture via a syringe and stirred for ca. 2 h. The solution was filtered and the white precipitate collected, washed with hexane and dried in vacuo. Yield: 0.150 g, 70%.

Anal. Calc. for $C_9H_{21}F_3InN_3$—$H_2O$: C, 29.9; H, 6.4; N, 11.6. Found: C, 29.9; H, 6.1; N, 11.5%.

$^1$H NMR (CD$_2$Cl$_2$, 298 K): δ 3.09-3.15 (br m, [6H], CH$_2$), 2.93 (m, [9H], Me), 2.72-2.82 (br m, [6H], CH$_2$), 2.19 (s, H$_2$O).

IR (Nujol, v/cm$^{-1}$): 3392 br (H$_2$O), 1669 (H$_2$O), 479, 462, 443 (In—F).

Colorless crystals were grown from the CH$_2$Cl$_2$ solution of the product upon slow evaporation.

Method 2:

[InCl$_3$(Me$_3$-tacn)] (Example 11, 0.060 g, 0.17 mmol) was suspended in 5 mL anhydrous CH$_2$Cl$_2$. The suspension was treated with [NMe$_4$]F (0.047 g, 0.51 mmol) and stirred at room temperature for 1 h. The [NMe$_4$]Cl by-product was removed by filtration. The resulting colorless filtrate was treated with 5 mL anhydrous hexane, forming a white precipitate which was isolated by filtration and dried in vacuo. Yield: 0.044 g, 76%.

Spectroscopic data as for Method 1.

Colourless crystals were grown from the CH$_2$Cl$_2$ solution of the product upon slow evaporation.

EXAMPLE 14

Synthesis of [InCl$_3$(BzMe$_2$-tacn)]

BzMe$_2$-tacn (0.125 g, 0.50 mmol) was added to a solution of InCl$_3$ (0.110 g, 0.50 mmol), 1:1, in dry CH$_2$Cl$_2$ (5-8 mL) at room temperature and stirred. After approximately 30 minutes some white precipitate had started to form, turning the mixture cloudy. After 2 h, stirring was stopped and the mixture was concentrated by removal of CH$_2$Cl$_2$, which caused further precipitation of the product. The white product was filtered from the yellow solution under nitrogen and was dried under vacuum for 2 h. Yield: 0.093 g, 40%.

Anal. Calc. for $C_{15}H_{25}Cl_3InN_3$: C, 38.5; H, 5.4; N, 9.0. Found C, 38.8; H, 5.8; N, 8.7%.

$^1$H NMR (CD$_3$CN, 298 K): 7.2-7.4 (m, [5H], ArH), 4.37 (s, [2H], Ar—CH$_2$), 3.45 (br, [2H], tacn-CH$_2$), 3.10 (br, [2H], tacn-CH$_2$), 2.80 (s, [6H], CH$_3$), 2.75 (br m, [2H], tacn-CH$_2$), 2.60 (br m, [2H], tacn-CH$_2$), 2.40 (br m, [2H], CH$_2$).

IR (Nujol, v/cm$^{-1}$): 289, 271 (In—Cl).

Crystals formed from the CH$_2$Cl$_2$ solution of the product stored in the freezer at −18° C.

EXAMPLE 15

Synthesis of [InF$_3$(BzMe$_2$-tacn)]

[InCl$_3$(BzMe$_2$-tacn)] (Example 14, 0.06 g, 0.10 mmol) was suspended in 5 mL anhydrous CH$_2$Cl$_2$. The suspension was treated with [NMe$_4$]F (0.03 g, 0.30 mmol) and stirred at room temperature for 1 h. The [NMe$_4$]Cl by-product was removed by filtration. The resulting colorless filtrate was treated with 5 mL anhydrous hexane, forming in a white precipitate which was isolated by filtration, washed with hexane and dried in vacuo. Yield: 0.02 g, 48%.

$^1$H NMR (CD$_3$CN, 298 K): 7.37 (m, [5H], ArH), 4.37 (s, [2H], Ar—CH$_2$), 3.08 (m, [6H], CH$_3$), 2.91 (m, [4H], tacn-CH$_2$), 2.80 (m, [4H], tacn-CH$_2$), 2.64 (m, [4H], tacn-CH$_2$).

IR (Nujol, v/cm$^{-1}$): 3450 v br (H$_2$O), 1651 (H$_2$O), 481, 463 (In—F).

Crystals were obtained by cooling the filtrate in the freezer.

EXAMPLE 16

$^{18}$F-Radiolabelling of [GaCl$_3$(BzMe$_3$-tacn)]

[GaCl$_3$(BzMe$_2$-tacn)] (Example 9; 1 mg, 2.36 μmol) was dissolved in 0.5 mL MeCN/0.1 mL H$_2$O. The solution was added to 0.4 ml of an aqueous solution containing [$^{18}$F] fluoride (100 to 400 MBq) and [$^{19}$F]KF (7.05 μmol), and the vial was left to stand at room temperature for 30 to 60 minutes. Subsequent HPLC confirmed 20 to 40% incorporation of $^{18}$F into the metal complex.

HPLC: Luna 5μ C18(2) 150×4.6 mm (Mobile phase A=50 mM ammonium acetate;

Mobile phase B=100% MeCN). Flow rate 1 mL/min.

0 min (10% B), 15 min (90% B), 20 min (90% B), 21 min (10% B), 26 min (10% B).

TABLE 1

Summary of NMR spectroscopic data.

| Complex | $\delta^{27}$Al/$^{71}$Ga/$^{115}$In/ ppm; ($w_{1/2}$/Hz) | $\delta^{19}$F{$^1$H} (ppm) | Solvent |
| --- | --- | --- | --- |
| [AlF$_3$(Me$_3$-tacn)] | 19.0 (60) | −176.1 | MeCN |
|  | 18.5 (52) | −169.9 | D$_2$O |
| [AlCl$_3$(Me$_3$-tacn)] | 34.5 (30) | — | CH$_2$Cl$_2$ |
| [AlBr$_3$(Me$_3$-tacn)] | 18.9 (80) | — | CH$_2$Cl$_2$ |
| [GaF$_3$(Me$_3$-tacn)] | 42.0 | −180.9 (two br q) | CH$_2$Cl$_2$ |
|  | (q, $^1J_{GaF}$ ~490 Hz) 44.6 (br q) | −173 (br) | D$_2$O |
| [GaCl$_3$ (Me$_3$-tacn)] | 93.9 (60) | — | CH$_2$Cl$_2$ |
| [GaBr$_3$(Me$_3$-tacn)] | −29.3 (180) | — | MeCN |
| [InF$_3$(Me$_3$-tacn)] | 64 | −215 (br) | MeCN |
|  | (q, $^1J_{InF}$ ~600 Hz) n.o. | −192.5 (br) | D$_2$O |
| [InCl$_3$(Me$_3$-tacn)] | 268 (750) | — | CH$_2$Cl$_2$ |
| [InBr$_3$(Me$_3$-tacn)] | n.o.$^a$ | — | MeCN |
| [AlF$_3$(BzMe$_2$-tacn)] | 20.3 (m) | −149.4 (m, F), −150.4 (m, 2F) | MeCN |
| [AlCl$_3$(BzMe$_2$-tacn)] | 36.5 (45) | — | CH$_2$Cl$_2$ |
| [AlBr$_3$(BzMe$_2$-tacn)] | 20.1 (35) | — | CH$_2$Cl$_2$ |
| [GaF$_3$(BzMe$_2$-tacn)] | 44.9 (q $^1J_{GaF}$ ~445 Hz) | −172.8 (br) | D$_2$O |
| [GaCl$_3$(BzMe$_2$-tacn)] | 92.8 (360) | — | MeCN |
| [InF$_3$(BzMe$_2$-tacn)] | n.o.$^a$ | −220 (br) | MeCN |
| [InCl$_3$(BzMe$_2$-tacn)] | 265 (2200) | — | MeCN |

$^a$n.o. = not observed

What is claimed is:

1. An imaging agent which comprises an $^{18}$F-labelled compound of Formula I:

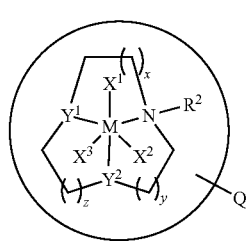

(I)

where:

Y$^1$ and Y$^2$ are independently O or NR$^1$, where R$^1$ is C$_{1-3}$ alkyl or —CH$_2$—Ar$^1$, wherein Ar$^1$ is C$_{5-12}$ aryl or C$_{3-12}$ heteroaryl;

X$^1$, X$^2$ and X$^3$ are independently $^{19}$F or $^{18}$F, with the proviso that at least one of X$^1$, X$^2$ and X$^3$ is $^{18}$F and at least one of the remaining X$^1$, X$^2$, and X$^3$ is $^{19}$F;

M is $Al^{3+}$, $Ga^{3+}$, $In^{3+}$, $Se^{3+}$, $Y^{3+}$, $Ho^{3+}$, $Er^{3+}$, $Tm^{3+}$, $Yb^{3+}$ or $Lu^{3+}$;

x, y and z are 1;

$R^2$ is $R^1$ or Q;

Q is -L-[BTM], and may be present or absent; when present it is either $R^2$ or is attached at one of the carbon atoms of the $-(CH_2)(CH_2)_x-$, $-(CH_2)(CH_2)_y-$ or $-(CH_2)(CH_2)_z-$ groups, where BTM is a biological targeting moiety;

wherein L is a synthetic linker group of formula $-(A)_m-$ wherein each A is independently $-CR^3_2-$, $-CR^3=CR^3-$, $-C\equiv C-$, $-CR^3_2CO_2-$, $-CO_2CR^3_2-$, $-NR^3CO-$, $-CONR^3-$, $-CR^3=N-O-$, $-NR^3(C=O)NR^3-$, $-NR^3(C=S)NR^3-$, $-SO_2NR^3-$, $-NR^3SO_2$, $-CR^3_2OCR^3_2-$, $-CR^3_2SCR^3_2-$, $-CR^3_2NR^3CR^3_2-$, a $C_{4-8}$ cycloheteroalkylene group, a $C_{4-8}$ cycloalkylene group, $-Ar^2-$, $-NR^3-Ar^2-$, $-O-Ar^2-$, $-Ar^2-(CO)-$, an amino acid, a sugar or a monodisperse polyethyleneglycol (PEG) building block, wherein each $R^3$ is independently chosen from H, $C_{1-4}$ alkyl, $C_{2-4}$ alkenyl, $C_{2-4}$ alkynyl, $C_{1-4}$ alkoxyalkyl or $C_{1-4}$ hydroxyalkyl;

m is an integer of value 1 to 20; and each $Ar^2$ is independently a $C_{5-12}$ arylene group, or a $C_{3-12}$ heteroarylene group.

2. The agent of claim 1, where Q is present.

3. The agent of claim 1, which is of Formula IA:

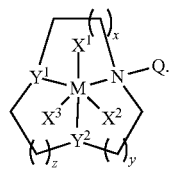

(IA)

4. The agent of claim 1, where $Y^1=Y^2=NR^1$.

5. The agent of claim 1, which is of Formula IB:

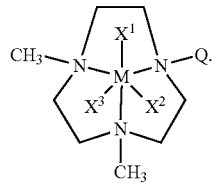

(IB)

6. A method of preparation of the agent of claim 1, which comprises reaction of a precursor of Formula II at room temperature with a supply of [$^{18}$F]-fluoride or [$^{18}$F]NaF, and in the presence of [$^{19}$F]-fluoride, in a suitable solvent:

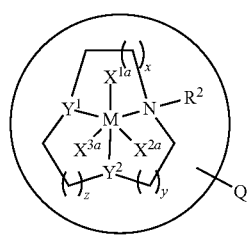

(II)

where M, $Y^1$, $Y^2$, x, y and z are as defined in claim 1; and $X^{1a}$, $X^{2a}$ and $X^{3a}$ are independently Br or Cl.

7. The method of claim 6, where the precursor is of Formula IIA:

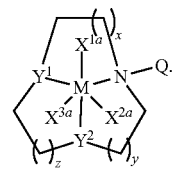

(IIA)

8. The method of claim 6, where the precursor is of Formula IIB:

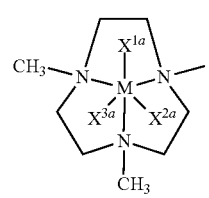

(IIB)

9. The method of claim 6, where $X^{1a}=X^{2a}=X^{3a}=Cl$.

10. A radiopharmaceutical composition which comprises the agent of claim 1, together with an aqueous biocompatible carrier, wherein the composition is in a form suitable for mammalian administration and has a pH range of 4 to 10.5.

11. A method of preparation of the agent of claim 1, which comprises reaction of a precursor of Formula II at room temperature with a supply of [$^{18}$F]-fluoride or [$^{18}$F]NaF, and in the presence of [$^{19}$F]-fluoride, in a suitable solvent:

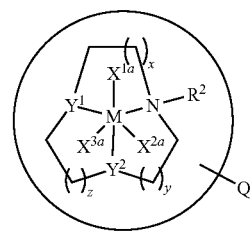

(II)

where M, $Y^1$, $Y^2$, x, y and z are as defined in claim 1; and $X^{1a}$, $X^{2a}$ and $X^{3a}$ are independently Br or Cl;

using an automated synthesizer apparatus.

12. The method of claim 11, where the automated synthesizer apparatus comprises a cassette which comprises the non-radioactive reagents necessary to carry out the method.

13. The method of claim 11, wherein the precursor is provided in sterile, lyophilized form.

14. A method of imaging the human or animal body which comprises generating an image of at least a part of said body to which the imaging agent of claim 1 has distributed using PET, wherein said agent has been previously administered to said body.

15. A method of imaging the human or animal body which comprises generating an image of at least a part of said body to which the composition of claim 10 has distributed using PET, wherein said composition has been previously administered to said body.

16. An imaging agent which comprises an $^{18}$F-labelled compound of Formula IA:

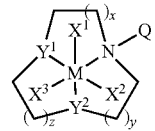
(IA)

where:

$Y^1$ and $Y^2$ are $NR^1$, where $R^1$ is $C_{1-3}$ alkyl or —$CH_2$—$Ar^1$, wherein $Ar^1$ is $C_{5-12}$ aryl or $C_{3-12}$ heteroaryl;

$X^1$, $X^2$ and $X^3$ are independently $^{19}$F or $^{18}$F, with the proviso that at least one of $X^1$, $X^2$ and $X^3$ is $^{18}$F and at least one of the remaining $X^1$, $X^2$, and $X^3$ is $^{19}$F;

M is $Ga^{3+}$ or $In^{3+}$;

x, y and z are 1;

Q is -L-[BTM], where BTM is a biological targeting moiety;
 wherein L is a synthetic linker group of formula $-(A)_m$- wherein each A is independently —$CR^3{}_2$—, —$CR^3$=$CR^3$—, —C≡C—, —$CR^3{}_2CO_2$—, —$CO_2CR^3{}_2$—, —$NR^3CO$—, —$CONR^3$—, —$CR^3$=N—O—, —$NR^3(C$=$O)NR^3$—, —$NR^3(C$=$S)NR^3$—, —$SO_2NR^3$—, —$NR^3SO_2$—, —$CR^3{}_2OCR^3{}_2$—, —$CR^3{}_2SCR^3{}_2$—, —$CR^3{}_2NR^3CR^3{}_2$—, a $C_{4-8}$ cycloheteroalkylene group, a $C_{4-8}$ cycloalkylene group, —$Ar^2$—, —$NR^3$—$Ar^2$—, —O—$Ar^2$—, —$Ar^2$—(CO)—, an amino acid, a sugar or a monodisperse polyethyleneglycol (PEG) building block;

wherein each $R^3$ is independently chosen from H, $C_{1-4}$ alkyl, $C_{2-4}$ alkenyl, $C_{2-4}$ alkynyl, $C_{1-4}$ alkoxyalkyl or $C_{1-4}$ hydroxyalkyl;

m is an integer of value 1 to 20; and each $Ar^2$ is independently a $C_{5-12}$ arylene group, or a $C_{3-12}$ heteroarylene group.

17. The agent of claim 16, which is of Formula IB:

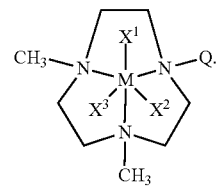
(IB)

18. A radiopharmaceutical composition which comprises the agent of claim 16, together with an aqueous biocompatible carrier, wherein the composition is in a form suitable for mammalian administration and has a pH range of 4 to 10.5.

19. The agent of claim 1, where M is $Ga^{3+}$ or $In^{3+}$.

* * * * *

UNITED STATES PATENT AND TRADEMARK OFFICE
CERTIFICATE OF CORRECTION

PATENT NO. : 11,135,322 B2
APPLICATION NO. : 14/373413
DATED : October 5, 2021
INVENTOR(S) : Rajiv Bhalla et al.

It is certified that error appears in the above-identified patent and that said Letters Patent is hereby corrected as shown below:

In the Claims

Claim 1, Column 25, Line 1; delete "$Se^{3+}$" and insert --$Sc^{3+}$--.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*